United States Patent
Hussein et al.

[11] Patent Number: 5,878,751
[45] Date of Patent: Mar. 9, 1999

[54] METHOD FOR TRANS MYOCARDIAL REVASCULARIZATION (TMR)

[75] Inventors: Hany Hussein, Costa Mesa; Stanislaw Sulek, Irvine, both of Calif.

[73] Assignee: Myocardial Stents, Inc., Costa Mesa, Calif.

[21] Appl. No.: 954,115

[22] Filed: Oct. 20, 1997

Related U.S. Application Data

[62] Division of Ser. No. 739,724, Nov. 7, 1996, Pat. No. 5,810,836.

[51] Int. Cl.$^6$ .................................................... A61B 19/00
[52] U.S. Cl. .............................................. 128/898; 606/7
[58] Field of Search ...................... 606/108, 185, 606/195, 198, 191, 7; 128/898; 623/1, 12, 9

[56] References Cited

U.S. PATENT DOCUMENTS

| | | | |
|---|---|---|---|
| 5,713,894 | 2/1998 | Murphy-Chutorian et al. | 606/7 |
| 5,782,823 | 7/1998 | Mueller | 606/7 |

*Primary Examiner*—Michael Buiz
*Assistant Examiner*—Kevin Truong
*Attorney, Agent, or Firm*—James G. O'Neill

[57] ABSTRACT

A stent for insertion into a heart wall for Trans Myocardial Revascularization (TMR) thereof. The TMR stent provides for the delivery of blood nutrients from a heart chamber into the heart wall and has an elongated body which may contain a cavity and openings through the elongated body from the cavity. The elongated body should be in fluid communication with the heart chamber. If a cavity and openings are provided, the openings are in fluid communication with the heart chamber, the cavity and the heart wall. The TMR stent may include an anchoring element integrally formed thereon for securing the TMR stent in the heart wall.

23 Claims, 13 Drawing Sheets

METHOD FOR TRANS MYOCARDIAL REVASCULARIZATION (TMR)

This is a division of application Ser. No. 08/739,724, filed Nov. 7, 1996 now U.S. Pat. No. 5,810,836.

TECHNICAL FIELD

This invention is generally directed to the fields of cardiac surgery and interventional cardiology, and particularly to mechanical devices and methods suited for improving blood flow to the heart muscle by Trans Myocardial Revascularization (TMR).

BACKGROUND OF THE INVENTION

Symptomatic occlusive coronary artery disease that does not respond to medical or interventional treatment is a major challenge for cardiac surgeons and cardiologists. The discovery of sinusoidal communications within the myocardium (Wearns, 1933) has motivated researchers to attempt various methods for myocardial revascularization based on the existence of this vascular mesh network. These methods aimed at the delivery of oxygenated blood to the vicinity of the sponge-like sinusoidal plexus in order to restore blood flow to the ischemic myocardium. Several investigators have attempted to deliver oxygenated blood directly from the left ventricle into the myocardial sinusoids by employing needle acupuncture to create transmural channels. Trans Myocardial Revascularization (TMR) has been employed clinically (Mirhoseini, 1991) by utilizing a $CO_2$ laser system for creating transmural channels in the left ventricular myocardium. These channels are typically 1 mm in diameter and extend throughout the wall thickness (15 to 20 mm) of the ventricle. It has been hypothesized that TMR works by providing a fluid conduit for oxygenated blood to flow from the endocardiac surface (heart chamber) to the myocardium inner layers thus providing oxygenated blood to myocardial cells without requiring coronary circulation; as in reptiles. Animal studies in the canine model have demonstrated the feasibility of this approach. In these studies, an increase in survival rate was demonstrated in dogs that had transmural channels and ligated coronary arteries.

While clinical studies have demonstrated improvements in patient status following TMR, histological studies indicate that the channels created for TMR tend to close shortly after the procedure. Randomized, prospective clinical trials are underway to examine the merit of TMR compared to medical treatment. In the meantime, research studies are being initiated to provide an understanding of the mechanism by which TMR actually works. It would be desirable to develop means for maintaining the patency of TMR channels created within the myocardium. Furthermore, it would be desirable to create channels for TMR without requiring the use of an expensive and bulky laser system such as the currently available $CO_2$ laser system. This invention provides the desired means for producing trans myocardial channels that are likely to remain patent, and that do not require laser application for generating these channels.

Specifically, the objective of the present invention is to generate needle-made channels or space in the ischemic heart wall, and to place in these channels (or space) an array of stents in order to provide improved means for supplying blood nutrients to ischemic myocardial tissue. Nutrients flow to the stented channels from the ventricular cavity, and diffuse from the side ports of the scent to the myocardial tissue through the needle-made channels. Our disclosed TMR approach of producing stented, needle-made, channels is supported by the recent scientific evidence (Whittaker et al, 1996) that needle-made transmural channels can protect ischemic tissue. Whittaker et al. assessed myocardial response at two months to laser and needle-made channels in the rat model which has little native collateral circulation. They found that channels created by a needle can protect the heart against coronary artery occlusion, and that these channels provide greater protection to ischemic tissue than channels created by laser. The limitation of needle-made channels is early closure (Pifarre, 1969). The disclosed stenting approach offers a possible solution to the early closure problem, while taking advantage of simple and effective needle-made channels for TMR.

SUMMARY OF THE INVENTION

This invention provides stent and needle means for creating and maintaining a patent lumen in the diseased myocardium. This stent provides a conduit for the flow of blood nutrients from the ventricular chamber to the intramyocardial vascular network. This stent can be used as the sole therapy or as an adjunctive therapy to other forms of TMR.

Revascularization of the myocardium can be achieved and maintained by creating stented, needle-made, channels within the myocardial tissue. These channels can allow blood nutrients within the left ventricular cavity to find direct access to ischemic zones within the ventricular wall independent of access through the coronary arteries.

Various configurations of the stent are disclosed; including flexible and rigid stents, screw stents, sleeve stents, and others. Manual or powered means are disclosed for the placement of the stent in the heart wall. The proximal end of the stent terminates at the epicardial surface and provides mechanical closure means to prevent stent detachment and leakage of blood from the ventricle. The stent is designed so as to maintain an adequate pressure gradient between the left ventricle and the myocardial tissue in order to maintain the flow from the ventricular cavity to the myocardial tissue of blood nutrients.

Furthermore, the disclosed TMR stent defines a cavity which can be pressurized during operation so as to enhance the flow of blood to myocardial tissue. Each stent can essentially operate as a mini-pump that is activated by myocardial contraction or by an external energy source.

Several embodiments of the stent are proposed, including the following: flexible spring, rigid sleeve, hollow screw, helical screw, and pumping (active) stent. The stent can be prestressed or made from memory metal in order to minimize the size of the stent during the insertion process.

DESCRIPTION OF PREFERRED EMBODIMENTS

Figure 1:
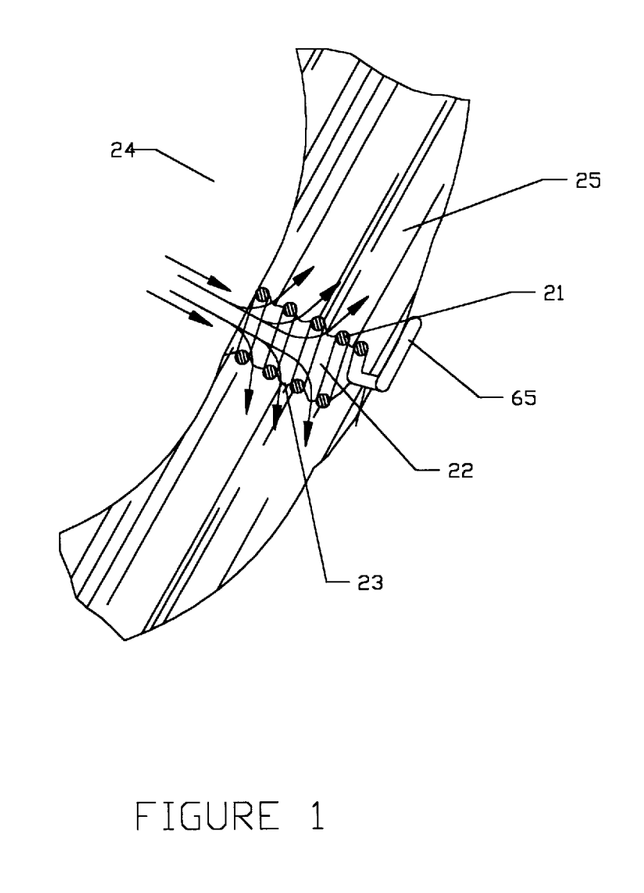
FIG. 1 is a cross-sectional view of a TMR stent inserted in a heart wall. The stent is configured as an expandable coil spring having an integral anchoring wire.

FIG. 1 shows a flexible TMR stent having a coil spring body 21 defining a cavity 22 and spacing 23 between the turns of said spring body. In this embodiment, blood nutrients flow from the heart chamber 24 to the heart wall 25 by passage through the coil spring cavity 22 and spacing 23. An anchoring wire 65 secures the stent to the heart wall.

Figure 2:
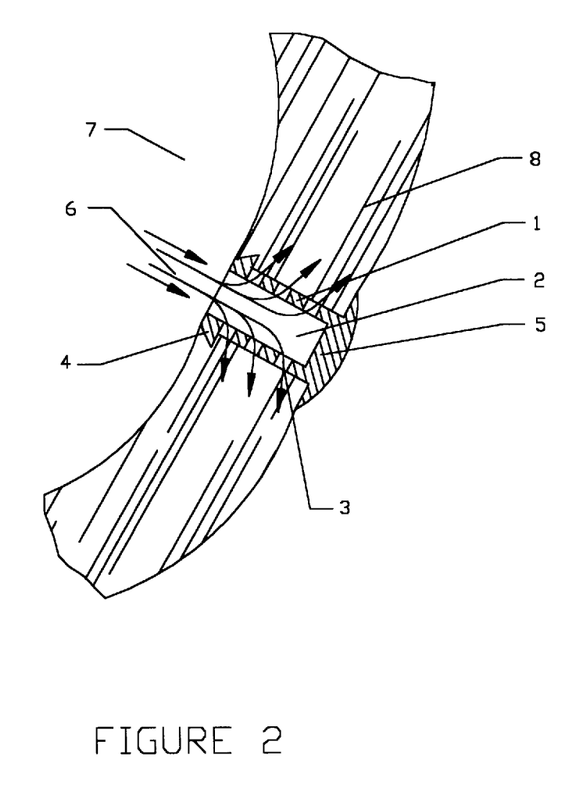
FIG. 2 is a cross-sectional view of a TMR stent having the configuration of a rigid sleeve having side ports.

FIG. 2 shows a TMR stent which comprises a tubular body 1, cavity 2, side ports 3, retainer 4, and closure 5. In this embodiment, blood nutrients 6 are transported from the heart chamber (ventricle) 7, through the cavity 2 and side ports 3, to the heart wall 8.

Figure 3:
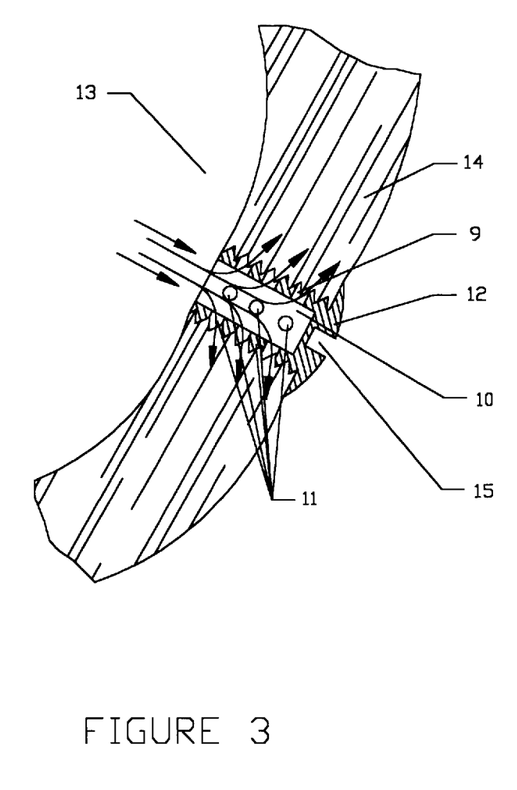
FIG. 3 is a cross-sectional view of a TMR stent having the configuration of a hollow screw with side ports.

FIG. 3 shows a TMR stent which is a hollow screw having a threaded body 9, cavity 10, side ports 11, closure 12, and slot 15. In this embodiment, blood nutrients flow from the heart chamber 13 to the heart wall 14 by passage through the cavity 10 and side ports 11.

Figure 4:
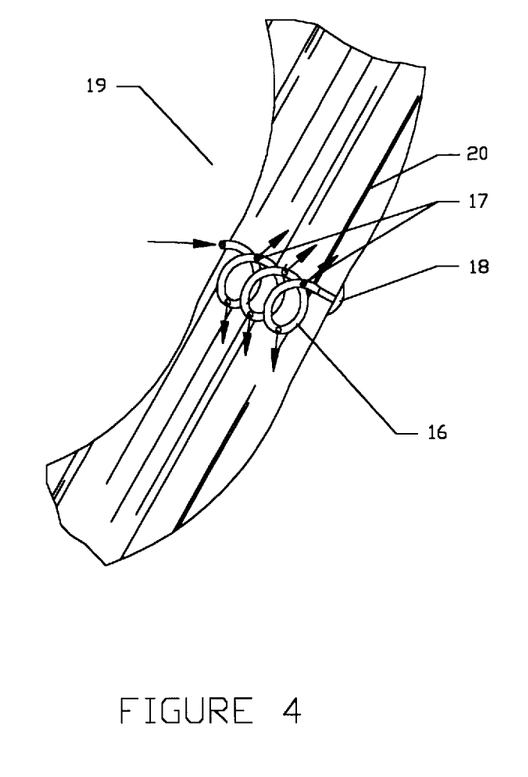
FIG. 4 is a cross-sectional view of a TMR stent having the configuration of a wire screw.

FIG. 4 shows a TMR stent which is a hollow wire screw having an elongated hollow coil body 16, side ports 17, and anchor 18. In this embodiment, blood nutrients flow from the heart chamber 19 to the heart wall 20 by passage through the hollow core of the wire 16 and side ports 17.

Figure 5:
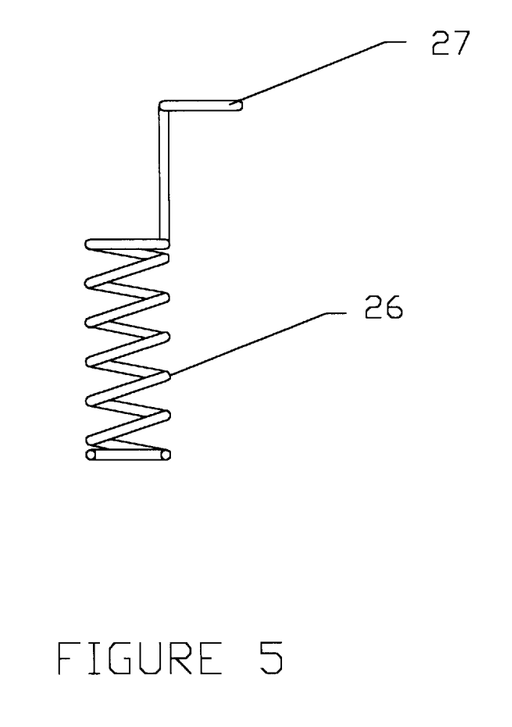
FIG. 5 is a cross sectional view of a flexible stent having an integral anchoring coil.

FIG. 5 shows a flexible stent having a coil body 26 and an anchoring coil 27 which is an integral part of the stent. The anchoring coil prevents detachment of the stent from the heart wall.

Figure 6:
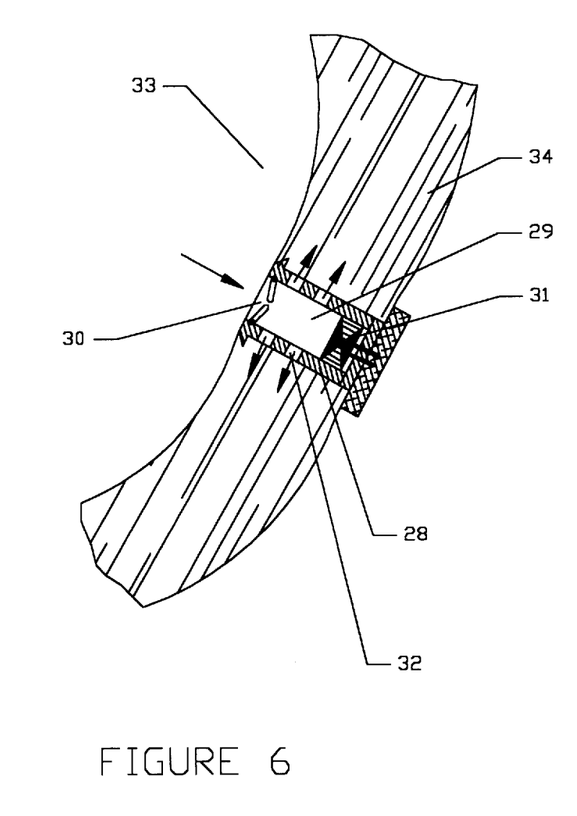
FIG. 6 is a cross-sectional view of a TMR stent having the configuration of a miniature pump.

FIG. 6 shows a TMR device having a cylindrical body 28 defining a cavity 29. A valve 30, pumping element 31, and side ports 32 are situated within the cavity 29. In this embodiment, blood nutrients flow from the heart chamber 33 to the pumping cavity 29. The valve 30 is activated and the pumping element 31 operates to displace the blood from the pumping cavity 29 through side ports 32 to the heart wall 34.

Figure 7:
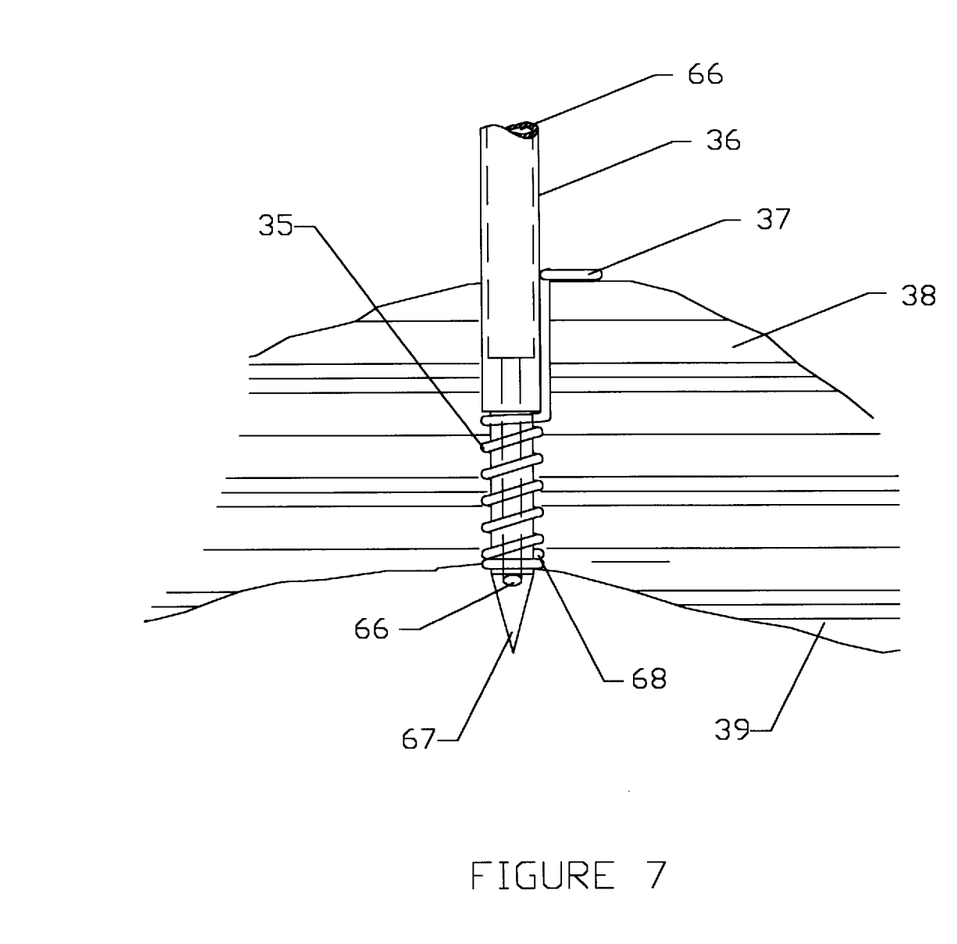
FIG. 7 shows a device and method for insertion into the heart wall of a TMR stent.

FIG. 7 shows the construction and method of use of a delivery device for creating a pathway in the heart wall and for placement of a myocardial stent in this pathway. In this figure, a needle obturator 36 carries a stent 35 having an anchoring wire 37. The obturator and stent are inserted through the heart wall 38 until the endocardiac surface is reached. Additional improvements include a channel 66 that is placed in the obturator body to provide indication that the obturator's distal end 67 has crossed the endocardiac surface 39.

Figure 8A:
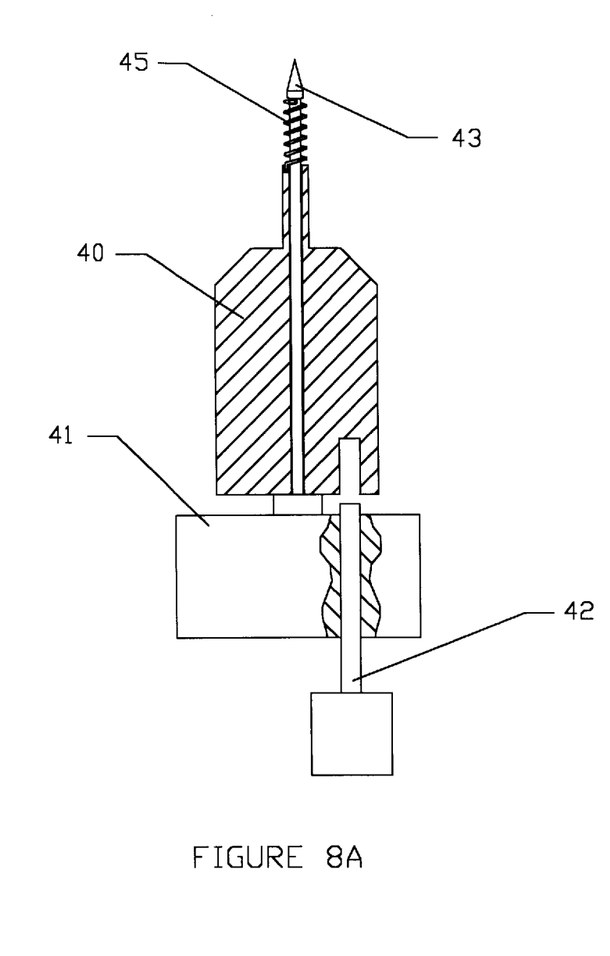
FIGS. 8A–8I illustrate an alternate TMR stent and a method for insertion of this TMR stent into a heart wall.
Figure 8B:
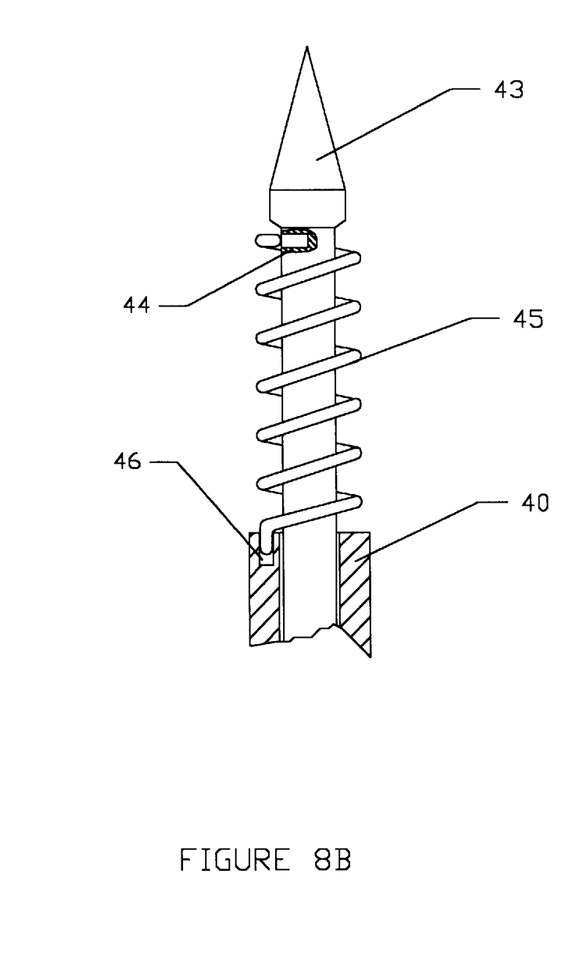
Figure 8C:
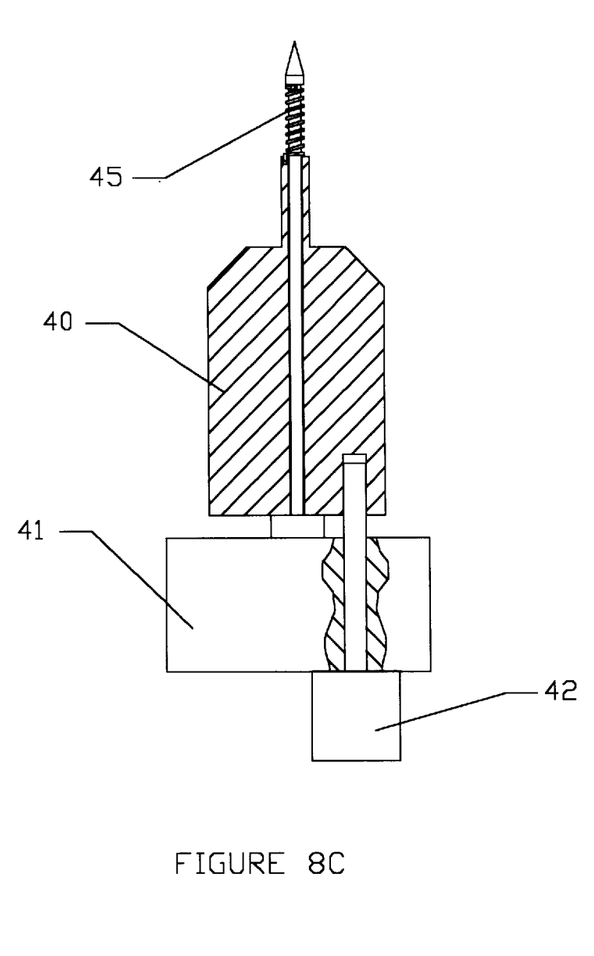
Figure 8D:
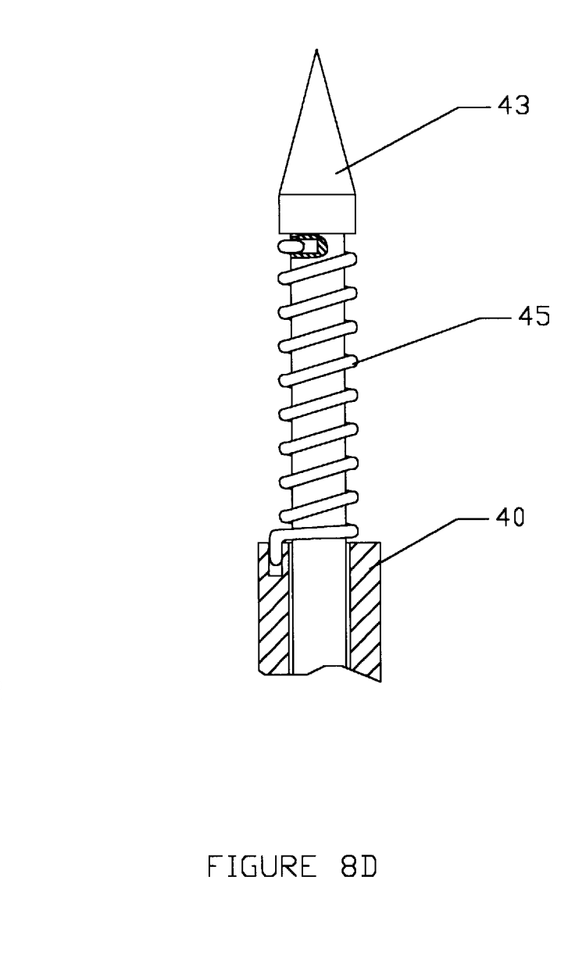
Figure 8E:
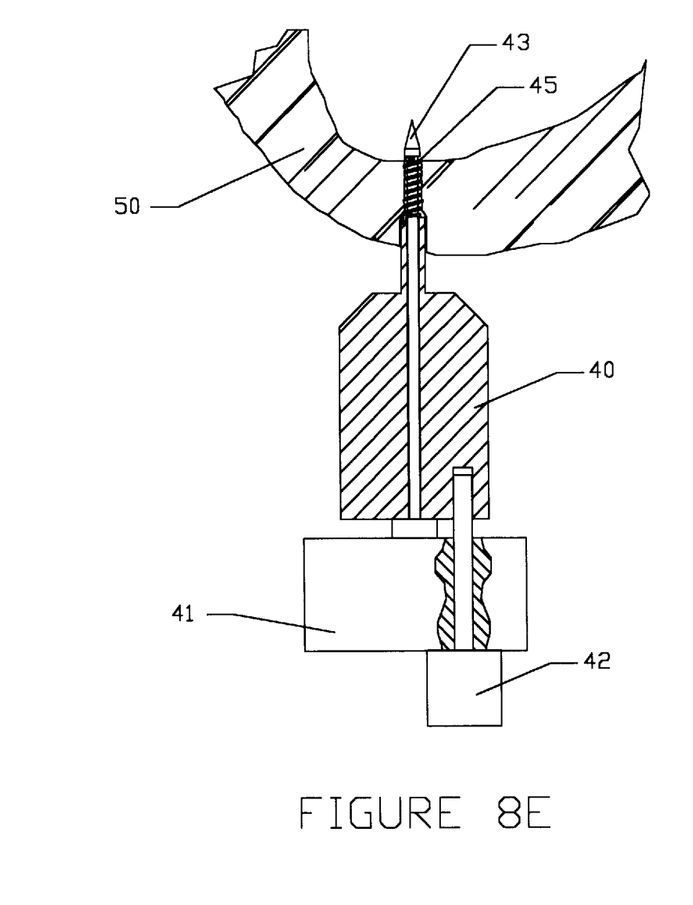
Figure 8F:
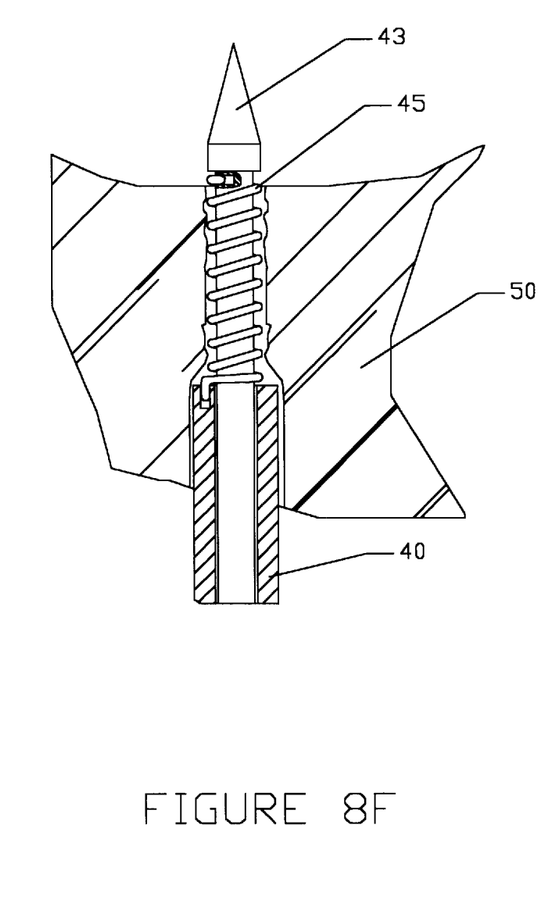
Figure 8G:
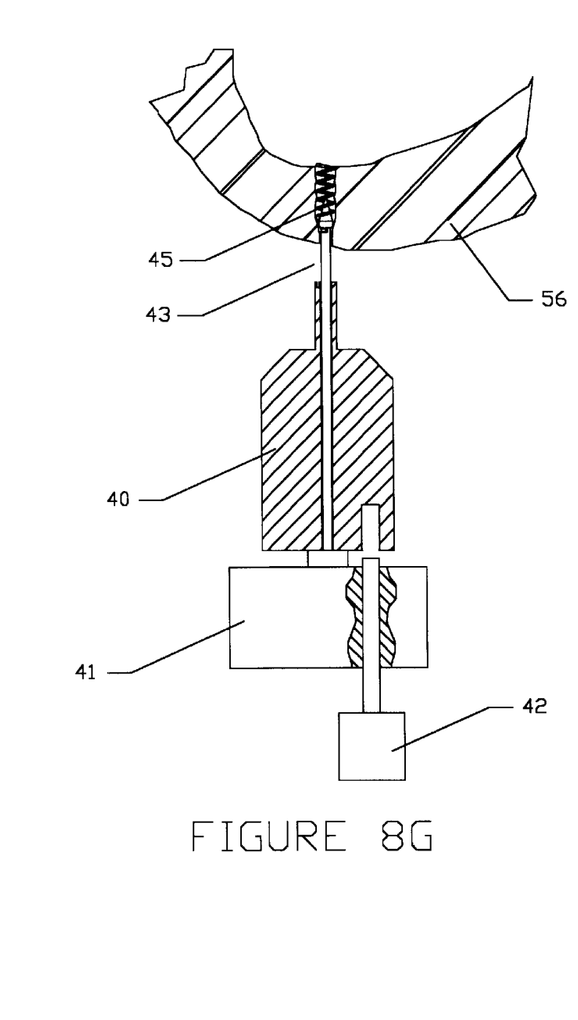
Figure 8H:
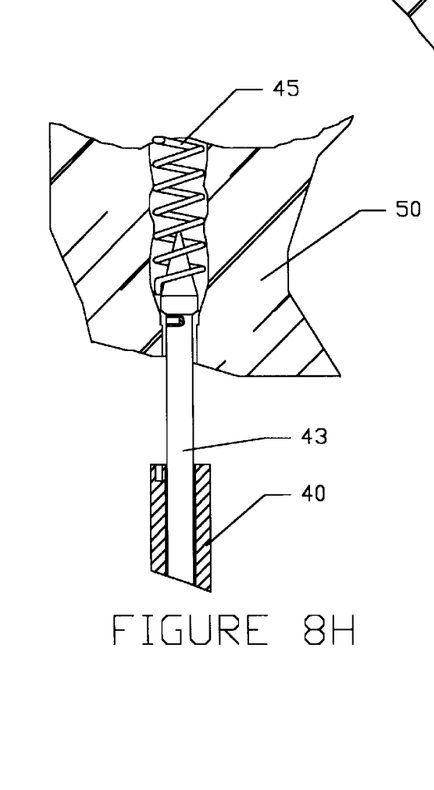
Figure 8I:
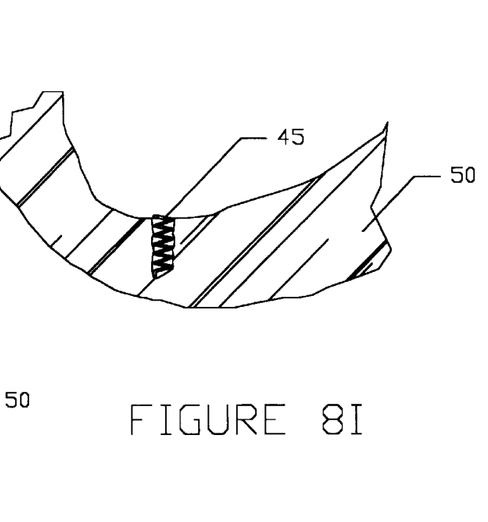

FIGS. 8A through 8I show the construction of an alternate TMR stent and a method of insertion by an alternate delivery system for placement of the alternate TMR stent in a heart wall. FIG. 8A shows a delivery system having a pin 40 and handle 41 having a locking device 42. An obturator 43 is mounted in the pin 40. The obturator 43 has a recess 44 (FIG. 8B) to engage the distal end of a TMR device 45. The pin 40 has a recess 46 (FIG. 8B) to engage the proximal end of a TMR device 45. The method of use involves the placement of a TMR device 45 over an obturator 43. The pin 40 is then rotated to create a radial stress on the TMR device 45 (FIG. 8D). The pin 40 is locked to the handle 41 (FIG. 8C). Advancement through the heart wall 50 of the obturator and TMR device 45 is achieved by pressing the obturator through the heart wall (FIGS. 8E, 8F). The pin 40 is released from handle 41 by withdrawing the locking device 42 (FIGS. 8G, 8H). This causes the TMR device 45 to be released from the obturator 43. The obturator 43 is then pulled back from the heart wall 50 leaving the TMR device 45 imbedded in the heart wall (FIG. 8I).

Figure 9:
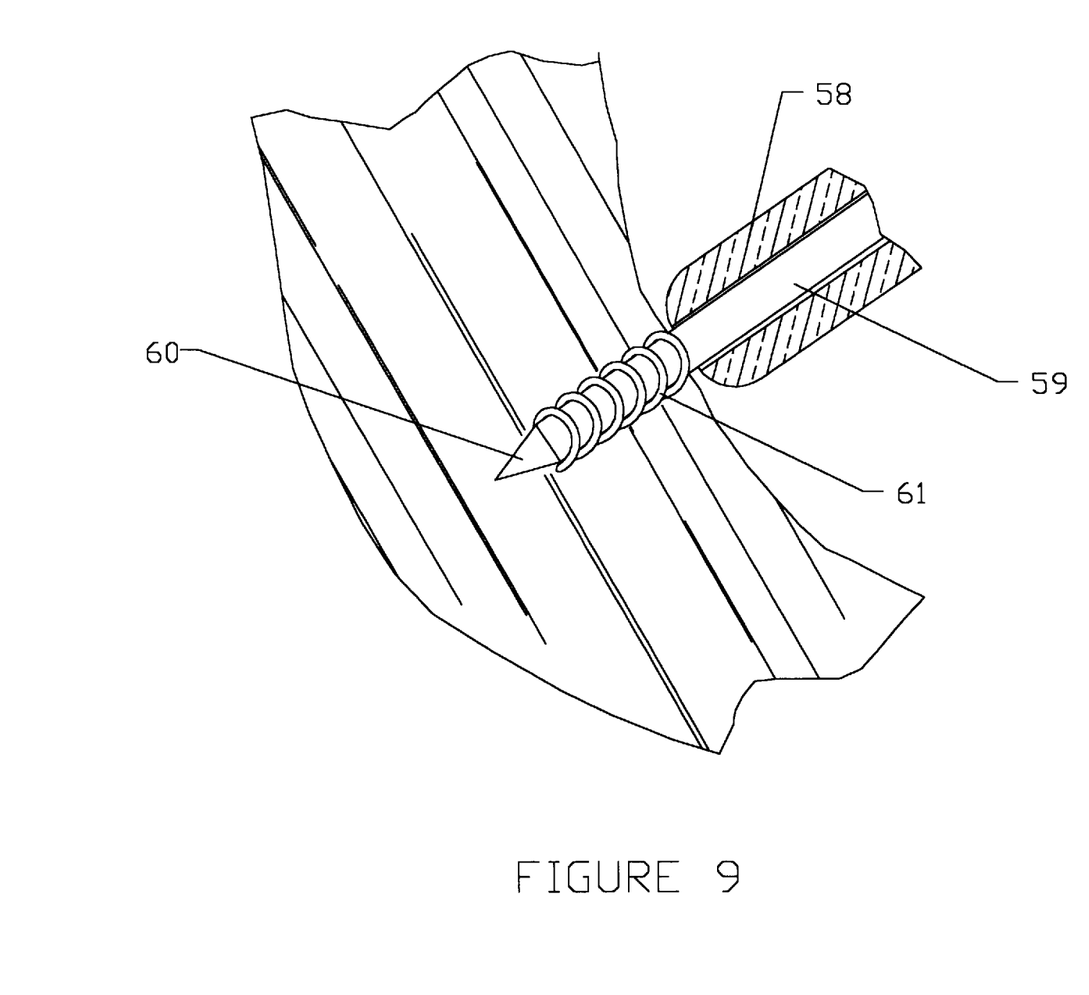
FIG. 9 shows a catheter device and method utilizing a percutaneous access for insertion of a TMR stent into a needle-made space within the heart wall.

FIG. 9 shows a catheter 58 having a slidable wire 59 which terminates at its distal end into a needle point 60. A stent 61 is mounted proximal to the needle point. Advancing the needle spreads the heart wall tissue and positions the stent into that tissue. Withdrawal of the needle releases the stent in the heart wall.

Figure 10:
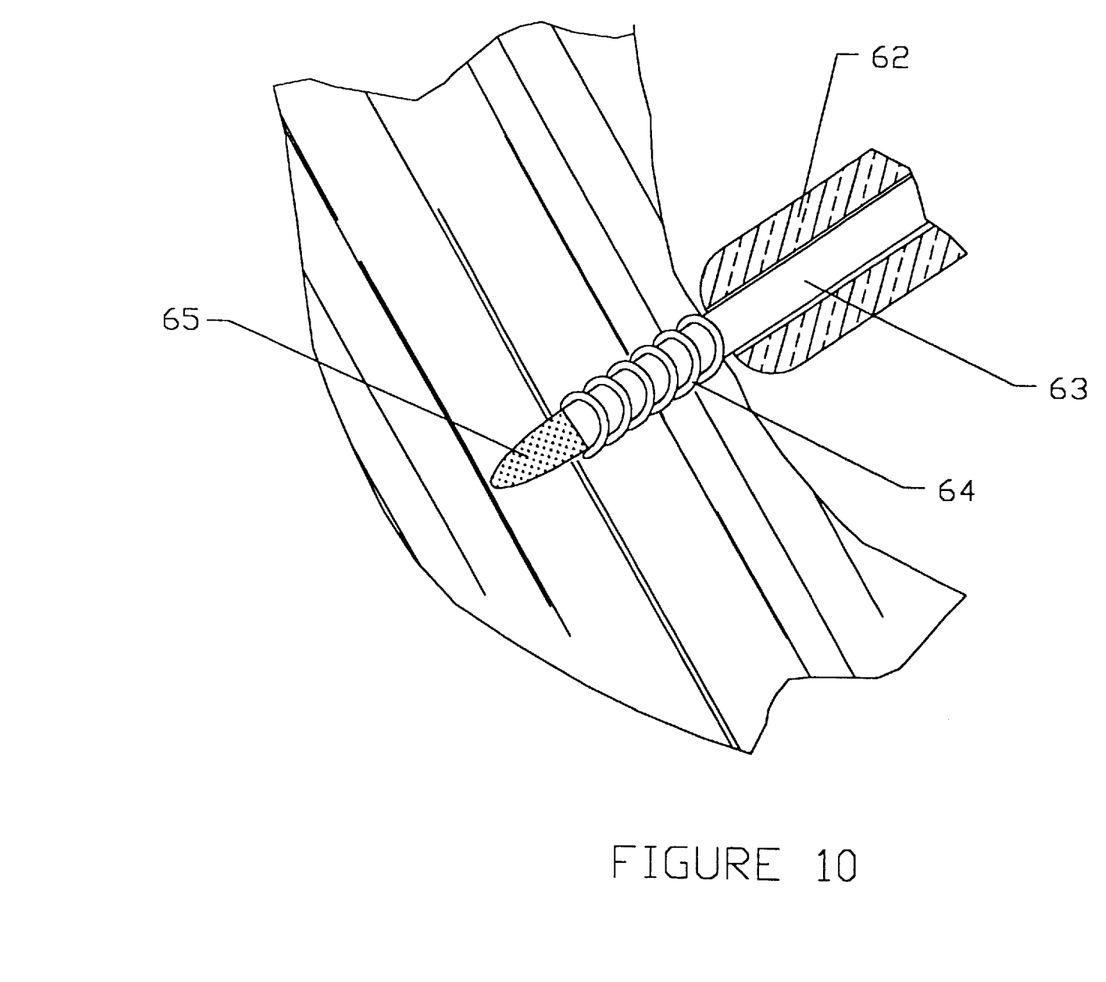
FIG. 10 shows an alternate catheter device and method utilizing a percutaneous access for creating a channel in the heart wall, and for insertion in this channel of a TMR stent.

FIG. 10 shows a catheter 62 which incorporates a slidable wire 63 that terminates at its distal end into a drill or other mechanical attachment 65 for making holes in the heart wall tissue. A stent 64 is mounted proximal to the drill 65 on the slidable wire 63. Advancing the drilling tool creates a channel in the tissue and positions the stent in this channel. Withdrawal of the drilling tool releases the stent in the heart wall.

The disclosed TMR device is expected to incorporate a cavity having a diameter in the range of 1–5 millimeters and a length in the range of 10–30 millimeters. The body of the TMR device is made of a bio-compatible material that resists clot formation; such as stainless steel. The TMR device may also be coated with a material, such as gold or carbon, that further reduces thrombus formation at the surface of the TMR device. The TMR device may also be made from carbon, gold, platinum, or other suitable materials.

The number of TMR devices used for each patient depends on the size of the device and the surface area of the heart segment that is being revascularized. For example, a small segment may require only one TMR device while a large segment may require 10 TMR devices to be implanted in the heart wall.

We claim:

1. A method for performing trans myocardial revascularization (TMR), comprising the steps of:
   a. identifying a portion of a heart wall that is targeted for treatment by TMR;
   b. obtaining access to the targeted portion of the heart wall; and
   c. inserting a TMR device into the targeted portion of the heart wall to aid in the formation of new blood vessels.

2. The method of claim 1, including the further step of creating a channel in the portion of the heart wall that is targeted for treatment by TMR.

3. The method of claim 2 wherein the created channel goes partially through the heart wall.

4. The method of claim 2 wherein the created channel goes entirely through the heart wall.

5. A method for the placement in a heart wall of a suitable trans myocardial revascularization (TMR) device to aid in the formation of new blood vessels, comprising the steps of:
   a. identifying a portion of the heart wall that is targeted for treatment by the TMR device;
   b. obtaining access to the targeted portion of the heart wall;
   c. forming a channel in the targeted portion of the heart wall; and d. inserting the TMR device into the channel formed in the targeted portion of the heart wall.

6. The method of claim 5, including the further step of turning the TMR device when inserting the TMR device into the channel in the targeted portion of the heart wall.

7. The method of claim 5, including the further step of pushing the TMR device when inserting the TMR device into the channel in the targeted portion of the heart wall.

8. The method of claim 5, including the further step of inserting the TMR device into the channel in the targeted portion of the heart wall by mechanical means.

9. The method of claim 5, including the further step of spreading the channel in the targeted portion of heart wall by use of an obturator, to facilitate the insertion of the TMR device into the channel in the targeted portion of the heart wall.

10. The method of claim 5, including the further step of facilitating the insertion of the TMR device into the channel in the targeted portion of the heart wall, by using an expandable pre-stressed TMR device.

11. The method of claim 5 wherein the created channel goes partially through the heart wall.

12. The method of claim 5 wherein the created channel goes entirely through the heart wall.

13. A method for performing trans myocardial revascularization (TMR), comprising the steps of:

a. identifying a portion of the heart wall that is targeted for treatment by a TMR device;

b. obtaining access to the targeted portion of the heart wall;

c. forming a channel in the targeted portion of the heart wall; and d. inserting the TMR device into the channel formed in the targeted portion of the heart wall by a mechanical means.

14. The method of claim 13 wherein the created channel goes partially through the heart wall.

15. The method of claim 14, including the further step of turning the mechanical means when inserting the TMR device into the channel in the targeted portion of the heart wall.

16. The method of claim 14, including the further step of pushing the mechanical means when inserting the TMR device into the channel in the targeted portion of the heart wall.

17. The method of claim 14, including the further step of causing the spreading of the channel in the targeted portion of heart wall by use of an obturator, to facilitate the insertion of the TMR device by the mechanical means into the channel in the targeted portion of the heart wall.

18. The method of claim 14, including the further step of facilitating the insertion of the TMR device by the mechanical means into the channel in the targeted portion of the heart wall, by using an expandable pre-stressed TMR device.

19. The method of claim 14 wherein the created channel goes entirely through the heart wall.

20. The method of claim 19, including the further step of turning the mechanical means when inserting the TMR device into the channel in the targeted portion of the heart wall.

21. The method of claim 19, including the further step of pushing the mechanical means when inserting the TMR device into the channel in the targeted portion of the heart wall.

22. The method of claim 19, including the further step of causing the spreading of the channel in the targeted portion of heart wall by use of an obturator, to facilitate the insertion of the TMR device by the mechanical means into the channel in the targeted portion of the heart wall.

23. The method of claim 19, including the further step of facilitating the insertion of the TMR device by the mechanical means into the channel in the targeted portion of the heart wall, by using an expandable pre-stressed TMR device.

* * * * *